United States Patent [19]

Stephenson

[11] 4,024,871

[45] May 24, 1977

[54] ANTIMICROBIAL SUTURES

[75] Inventor: Martin Stephenson, Peterborough, Canada

[73] Assignee: Ethicon, Inc., Somerville, N.J.

[22] Filed: July 23, 1975

[21] Appl. No.: 598,459

[52] U.S. Cl. .......................... 128/335.5; 424/16.28
[51] Int. Cl.² .................. A61L 17/00; A61K 27/12
[58] Field of Search ................ 128/335.5, 334 R; 424/16, 22, 28

[56] References Cited

UNITED STATES PATENTS

| | | | |
|---|---|---|---|
| 2,751,910 | 6/1956 | Howes | 128/335.5 |
| 3,454,011 | 7/1969 | Wagner | 128/335.5 |
| 3,545,439 | 12/1970 | Duncan | 128/260 |
| 3,674,901 | 7/1972 | Shepherd et al. | 128/335.5 |
| 3,737,521 | 6/1973 | Born | 424/22 |
| 3,896,813 | 7/1975 | Kurtz | 128/335.5 |

Primary Examiner—Dalton L. Truluck
Attorney, Agent, or Firm—Wayne R. Eberhardt

[57] ABSTRACT

Multifilament suture strands are impregnated with an antimicrobial agent and top coated with a segmented polyurethane polymer. The coated sutures possess antimicrobial properties which are retained during use over extended periods of time.

16 Claims, 1 Drawing Figure

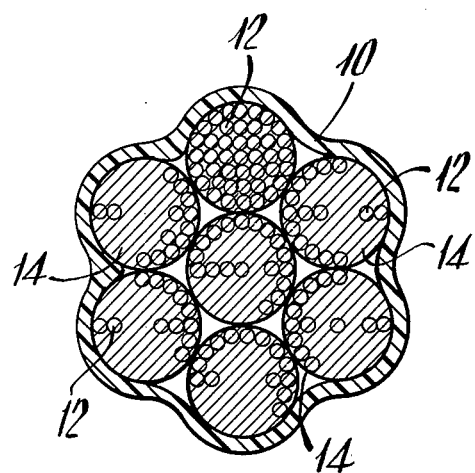

ANTIMICROBIAL SUTURES

BACKGROUND OF THE INVENTION

1. Field of Invention

This invention relates to surgical sutures, and more particularly to sutures which have been treated to render them antimicrobial.

2. Description of Prior Art

The need for antimicrobial sutures to reduce or eliminate the incidence of wound infection has long been recognized. It has been suggested to impregnate sutures with antimicrobial agents which were only slightly soluble and would leach from the suture over a period of several weeks. It has also been suggested to use hydrophilic binders to hold more soluble antimicrobial agents in the suture. Other methods for chemically bonding selected antimicrobial agents to the suture material have also been proposed.

The following references are illustrative of the prior art methods and compositions which have been proposed for antimicrobial sutures. The list is not exclusive and other related references may be known to those skilled in the art.

U.S. Pat. No. 861,231 (7-23-07) Microbiocidal sutures containing an insoluble antiseptic salt such as silver iodide.

U.S. Pat. No. 1,741,893 (12-31-29) A non-capillary, waterproof and bacteriostatic suture treated with an aluminum salt such as aluminum acetate.

U.S. Pat. No. 2,751,910 (6-26-56) Suture impregnated with an antibacterial agent and a wax or vinyl chloride/vinylidene chloride binder.

U.S. Pat. No. 3,317,376 (5-2-67) Fabrics impregnated with aqueous solutions of sodium phenolate, sodium tetraborate, glycerine and phenol.

U.S. Pat. No. 3,388,704 (6-18-60) Microbiocidal sutures containing quatenary ammonium salts.

U.S. Pat. No. 3,401,005 (9-10-68) A suture treated with N-hydroxymethyl lactam followed by treatment with a hologen-containing germicidal agent.

U.S. Pat. No. 3,536,437 (10-27-70) Fibers treated with reactive dyes containing ionogenic groups are acidified, then reacted with cationic bactericidal agents.

U.S. Pat. No. 3,632,416 (1-4-72) and 3,674,901 (7-4-72) Sutures coated with hydrophilic acrylate or methacrylate polymers containing a small amount of an antibacterial agent, or polymer-coated sutures treated with antibacterial agents.

U.S. Pat. No. 3,642,003 (2-15-72) A nitrogenous, amphoteric, organic suture bonded to cationic or anionic germicidal surface active agents such as quaternary ammonium salts or organic sulfonates.

Canadian Pat. No. 916,052 (12-5-72) Substantially insoluble high molecular weight germicidal salts are formed within a suture by reacting anionic and cationic agents in situ.

British Pat. No. 1,248,513 (10-6-71) Suture coated with hydrophilic polymer, e.g., glycerol or glycol-monomethacrylate or acrylate with antimicrobial agent applied to suture, before, with or after polymer coating.

An antimicrobial suture should demonstrate an effective level of antimicrobial activity over a period of at least 24 hours, and preferably longer, when implanted in animal tissue. The suture must be non-toxic and non-irritating to animal tissue. The treated suture should retain flexibility, strength and good handling and knotting properties characteristic of untreated sutures. It is accordingly an object of the present invention to provide an antimicrobial suture possessing these and other desirable properties as will be apparent from the ensuing description and claims.

SUMMARY

Antimicrobial sutures having long-lasting antimicrobial properties and desirable physical properties are obtained by impregnating a multifilament suture with a solution of an antimicrobial agent, drying the suture, and coating the surface of the impregnated suture with a segmented polyurethane polymer.

DESCRIPTION OF DRAWING

The FIGURE is an enlarged cross-sectional view of a coated multifilament antimicrobial suture strand.

DESCRIPTION OF PREFERRED EMBODIMENTS

The antimicrobial sutures of the present invention are characterized by a multifilament suture structure impregnated throughout with an antimicrobial agent and surface coated with a substantially continuous covering of a segmented polyurethane polymer.

With reference to the FIGURE, there is illustrated a cross-sectional view of a seven strand braided silk suture. The interstices between strands and between individual filaments 12 within strands contain antimicrobial agent 14 which is distributed substantially throughout the suture. The impregnated suture is surface coated with layer 10 of a segmented polyurethane which forms a substantially continuous and uniform covering over the suture without any substantial penetration into the suture strand.

The sutures which may be treated in accordance with the present invention includes any multifilament suture of natural or synthetic origin. Since the antimicrobial agent is not required to interact with the suture material as a condition of use, there are no limitations on suture compositions. Typical suture materials include silk, cotton, linen, polyolefins such as polyethylene and polypropylene, and polyesters such as polyethylene terephthalate and homopolymers and copolymers of hydroxycarboxylic acid esters. In addition, the sutures may be braided, twisted, or covered, and may be of a wide range of sizes in accordance with the standards set forth in the *U.S. Pharmacopeia*, Vol. XIX.

The antimicrobial agents useful in the practice of the present invention may be any anionic, cationic or non-ionic compound which is preferably water soluble. Inert solvents other than water, particularly alcohols, can be used with compatible antimicrobial compounds if necessary or desirable to achieve impregnation of the suture. Since the antimicrobial compound and solvent are not required to react with the suture material as a condition of use, there are no limitations on the composition of the antimicrobial compound or solvent other than mutual compatibility, i.e., that there is no adverse interaction between the suture, the solvent, and/or the antimicrobial agent. Representative water soluble antimicrobial agents include but are not limited to tetracycline hydrochloride, neomycin sulfate, chloramphenicol, streptomycin sulfate, potassium penicillin, polymixin B sulfate, oxytetracycline hydrochloride, gentamycin sulfate, sodium cephalothin, nitrofurazone, rifamycin, benzethonium chloride, sodium oxacillin, dihydrostreptomycin sulfate, disodium carbenicillin, and sodium furadantin.

The antimicrobial agent is applied to the suture by impregnating the suture with a dilute solution of the antimicrobial agent in a suitable solvent, and thereafter drying the impregnated suture to remove the solvent and leave a residue of antimicrobial agent distributed substantially throughout the suture structure. The concentration of antimicrobial agent within the suture may be from about 0.2 to 5 percent by weight, and preferably is from 0.5 to 2 percent, although concentrations outside these ranges can be used with good results. Antimicrobial solutions at concentrations of from about 2 to 15 percent by weight, and preferably 5 to 10 percent by weight are generally suitable for impregnation of the suture to deposit the desired concentration of antimicrobial agent within the suture.

The suture may be impregnated with the antimicrobial solution by any convenient method such as dipping, spraying, or soaking. The impregnated suture may be dried over hot rolls, in a warm air oven, by a continuous stream of warm air, or by any other convenient method. Drying temperatures and times are selected to avoid degradation of the suture material or antimicrobial compositions. In general, temperatures of 80°–100° C give rapid drying with no adverse effect on either the suture or the antimicrobial compound. In a preferred embodiment, the suture is impregnated and dried in a continuous process wherein the suture strand is passed through an impregnating bath followed by drying in warm air.

The segmented polyurethane useful in the practice of the present invention are those of the spandex type described in several patents among which are U.S. Pat. Nos. 2,929,804, 2,953,839, 2,957,852, 3,040,003, 3,071,557, 3,097,192 and 3,428,711, which patents are incorporated herein by reference. Such segmented polyurethane elastomers are comprised of "soft" segments, derived from polymers having a melting point below about 50° C and a molecular weight of above about 600, and "hard" segments, derived from a crystalline polymer having a melting point above about 200° C and a molecular weight in the fiber-forming range. The segmented polyurethanes are characterized by the recurring linkage —O—CO—NH—, with a substantial number of the urethane nitrogens joined to radicals, usually aromatic, which are further attached to a ureylene residue —NH—CO—NH—. Generally speaking, these segmented polyurethanes are prepared from hydroxyl-terminated prepolymers such as hydroxyl-terminated polyethers and polyesters of low molecular weight. Reaction of the prepolymer with a stoichiometric excess of organic diisocyanate, preferably an aromatic diisocyanate, produces an isocyanate-terminated polymeric intermediate, which may then be chain-extended with a difunctional, active hydrogen-containing compound, such as water, hydrazine, organic diamines, glycols, dihydrazides, amino-alcohols, etc.

From a standpoint of commercial availability, the preferred hydroxyl-terminated prepolymers are the polyether glycols, polyester glycols, and mixtures thereof. The polyether glycols may contain a single type of linkage, such as in the poly (alkylene oxide) glycols, or may have more than one type of linkage, as in the polyoxythiaalkylene glycols and in the polyether-ester glycols. Even where the linkages are the same, the composition may be a copolymer, such as copolyether prepared from a mixture of glycols. The polyether glycols may be substituted with halogen, alkyl, and similar groups, which do not interfere with the subsequent polymerization reactions. Representative polyethers which may be used include the poly (alkylene oxide) glycols, such as polyethylene glycol, polypropylene glycol, and polytetramethylene ether glycol, and the polyacetals, such as polydioxolane and polymers from the reaction of formaldehyde with hexamethylene glycol. For the purposes of this invention, the preferred polyether glycols include polytetramethylene ether glycol and glycols of polytetramethylene ether having urethane and/or ester groups in the polymer chain.

The polyester glycols may be prepared by reacting dibasic acids, esters, or acid halides with a molar excess of monomeric glycol, as is well known in the art. Suitable glycols are the polymethylene glycols, such as ethylene, propylene, pentamethylene, hexamethylene, decamethylene glycols; substituted polymethylene glycols such as 2-ethyl-2-methyl-propanediol, and cyclic glycol such as cyclohexnediol. These glycols may be reacted with the proper molar ratio of aliphatic, cycloaliphatic, or aromatic acids of their ester-forming derivatives to produce low molecular weight polymers. Suitable acids for preparing polyesters and/or copolyesters include carbonic, adipic, sebacic, terephthalic, and hexahydroterephthalic acids. Mixtures of glycols and/or mixtures of acids or acid derivatives to form copolyesters may also be employed. The alkyl and halogen substituted derivates of these acids may also be used. An ether containing glycol such as triethylene glycol, may be used to produce polyether-ester glycols. It will be apparent that polyester glycols derived from lactones of hydroxy acids may also be used.

The hydroxyl-terminated soft segment is generally reacted with an organic diisocyanate which is preferably an aromatic diisocyanate, as indicated hereinabove. Suitable aromatic diisocyanates include p-phenylene diisocyanate, 4,4'-biphenylene diisocyanate, p,p'-methylenediphenyl diisocyanate, and p,p'-isopropylidenediphenyl diisocyanate. Aliphatic and cycloaliphatic diisocyanates, for example, 4,4'-methylenedicyclohexyl diisocyanate, are also suitable. The diisocyanates may contain other substituents, although those which are free from reactive groups other than the two isocyanate groups, are ordinarily preferred. The organic diisocyanate is not critical for this invention, and any of these disclosed in the prior art pertaining to spandex may be used.

The difunctional, active hydrogen containing compounds suitable as chain extenders include a wide variety of compounds, as indicated hereinabove. Organic diamines are preferred. Suitable diamines include ethylenediamine, tetramethylenediamine, 1,2-propylenediamine, m-xylenediamine, p-xylenediamine, cyclohexylenediamine, piperazine, and many others. Symmetrical aliphatic diamines are preferred, but aromatic diamines, e.g., p-phenylenediamine and p,p'-methylenedianiline, may be used.

The polymerization reaction is conducted in a suitable polar solvent such as N,N-dimethylacetamide to yield a viscous solution of segmented polyurethane. Polymerization procedures are described in detail in the above enumerated references and illustrated by the following Example.

EXAMPLE I

Polytetramethylene ether glycol of molecular weight about 1800 and p,p'-methylenediphenyl diisocyanate are intimately mixed in the ratio of 1.7 mols of diisocyanate per mol of polyether glycol and held about 90 to 100 minutes at 80°–90° C to yield an isocyanate-terminated polyether. The isocyanate terminated polyether is cooled and dissolved in N,N-dimethylacetamide to give a mixture containing 45 percent solids. This mixture is thoroughly agitated for 15 minutes and is conducted to a chamber in which (1) a stoichiometric amount of a mixture consisting of 80 mol percent ethylenediamine and 20 mol percent 1,3-cyclohexylenediamine in additional dimethylacetamide and (2) about 7 mol percent diethylamine (based on total diamines) in dimethylacetamide are added with strong agitation. The mixture is held at a temperature of about 100° C for 2–3 minutes. The resulting solution of segmented polyurethane contains approximately 36 percent solids and has a viscosity of about 1800 poises at 40° C. The polymer has an intrinsic viscosity of 1.15, measured at 25° C in hexamethylphosphoramide at a concentration of 0.5 gram per 100 ml. of solution. The concentration of the polymer was adjusted to five percent by weight by the addition of N,N-dimethylacetamide, and the resulting solution used to coat the sutures for in vitro and in vivo testing hereinafter described.

The segmented polyurethane coating is applied to the antimicrobial-impregnated suture from a solution containing from about 2 to 20 percent by weight, and preferably 3 to 10 percent by weight polymer in a suitable solvent such as N,N-dimethylacetamide. The concentration of polymer in the solution is not critical, but it is preferred to have the maximum concentration consistent with uniform application as a coating. As the polymer concentration is increased above about 20 percent by weight, the higher viscosity of the solution makes uniform coating difficult. As the concentration is decreased below about 2 percent by weight, multiple passes are required to build up a coating of suitable weight, and there is a tendency for the lower viscosity solution to penetrate into the interstices of the suture and cause a stiffening effect.

The polymer coating may be applied by dipping, spraying, wiping, roller coating, or other convenient methods. The sutures are preferably coated with from about 3 to 20 percent by weight of segmented polyurethane polymer, and most preferably with from 5 to 10 percent by weight. At least about 2 percent by weight is required to control the migration of antimicrobial agent from the suture to the surrounding tissue, and more than about 20 percent is generally unnecessary and may result in stiffening of the suture and significant enlargement of suture diameter.

In a preferred embodiment, the antimicrobial impregnated suture is coated in a continuous process by passing the suture through a solution of polymer followed by drying with warm air to remove the solvent. When using a 5 to 10 percent solution of polymer, 3 to 6 applications may be necessary to deposit from 5 to 10 percent by weight of polymer on the suture.

The resistance of sutures to loss of antimicrobial activity by aqueous leaching in vitro was determined by the following test procedure.

Suture samples were extracted for various periods of time with distilled water by placing approximately 30 cm of suture in a bottle with 400 ml of distilled water. The bottle was clamped and slowly rotated on a washwheel for the designated time period.

Residual antimicrobial activity after increasing times of extraction was determined by the following procedure. Plates of tryptic soy agar were streaked with the organism Bacillus subtilis ATCC 19659 and incubated overnight at 37° C. Cells were washed from the surface by means of glass beads and saline to obtain a bacterial suspension. The optical density of each suspension was adjusted to 0.1. Tubes of tryptic soy broth + 0.4% Ion Agar 2 S culture media were equilibrated to a temperature of 45°–50° C in a water bath. 2.5 mil bovine serum and 0.25 ml of the adjusted bacterial suspension were pipetted into 25 ml of the culture media and mixed by slow vortexing or by hand. Eight milliliters of these seeded media were transferred to each plate and allowed to cool. 1.5 centimeter pieces of test sutures sterilized by cobalt 60 radiation were then placed on the agar and incubated for 24 hours at 37° C. After incubation, measurements were taken of the total zone width at right angles to the longitudinal axis of the suture, including the suture diameter.

In the following examples, a braided polyester suture was impregnated with the indicated antimicrobial agent and coated with the polymer solution of Example I. In vitro test results on coated and uncoated suture were as follows:

TABLE I

| | | | IN VITRO TEST | | | | | |
| | | | | Zone of Inhibition (cm) after Water Extraction | | | | |
| Example | Antimicrobial | | Polymer Coating* | 0 hr. | 2 hrs. | 4 hrs. | 6 hrs. | 18 hrs. |
| --- | --- | --- | --- | --- | --- | --- | --- | --- |
| II | 1.5% | Tetracycline hydrochloride | 5.4% | 2.5 | — | — | — | 1.0 |
| | | | 0 | 3.7 | — | — | — | 0 |
| III | 0.5% | Neomycin sulfate | 5.6 | 1.6 | 1.3 | 1.0 | 0.9 | 0.7 |
| | | | 0 | 2.0 | 0 | 0 | 0 | 0 |
| IV | 1.6% | Chloramphenicol | 6.0 | 2.5 | 0.3 | 0 | 0 | 0 |
| | | | 0 | 2.7 | 0 | 0 | 0 | 0 |
| V | 0.7% | Streptomycin Sulfate | 11.6 | 1.2 | 0.6 | 0 | 0 | 0 |
| | | | 7.7 | 0.9 | 0.8 | 0 | 0 | 0 |
| | | | 0 | 1.5 | 0 | 0 | 0 | 0 |
| VI | 1.3% | Potassium Penicillin | 5.5 | 2.9 | 2.4 | 2.1 | 1.9 | 1.5 |
| | | | 0 | 3.3 | 0 | 0 | 0 | 0 |

* Percent on weight of suture

The performance of the coated sutures in vivo and the resistance of the suture to loss of antimicrobial activity during implantation was determined by the following test procedure:

Healthy young adult Sprague-Dawley rats were anesthetized and prepared for surgery. Under sterile conditions, a 10 cm length of a sterile, coated antimicrobial-impregnated suture was inserted with a small hemostat through a small (0.5 cm) incision in the dorsal subcutis on the right side of the spinal column. In a similar fashion, a strand of uncoated, antimicrobial impregnated suture control was inserted on the left side and the incisions were closed with Michel clips. Two animals per implantation period were employed.

After 1, 3, 7, 14, 21 and 28 days of implantation, the animals were sacrificed, the dorsal skin was dissected, and the suture removed with a pair of dry, sterile forceps. Using a fresh set of dry sterile forceps for each suture strand, about 1 cm was cut off both ends of the recovered strand and the severed ends were discarded. The purpose of this was to avoid "end effects". Pieces approximately 1.5 cm long were cut from the remaining strand and, without sterilization, tested for residual antimicrobial activity by the standard procedure described above using B. subtilis as the test organism.

In the following examples, the sutures evaluated were the braided polyester sutures prepared for in vitro testing in Examples II, III, IV and V. Test suture (a) in each example was impregnated with the indicated antimicrobial agent and coated with a polyurethane polymer, while control suture (b) was similarly impregnated but uncoated.

TABLE II

| | | IN VIVO TEST | | | | |
| | | Zone of Inhibition (cm) after Period of Implantation | | | | |
| Example | Antimicrobial | 1 day | 3 days | 7 days | 14 days | 21 days |
|---|---|---|---|---|---|---|
| VIII | a. tetracycline hydrochloride | 0.7 | 0.7 | 0.8 | 0.6 | 0.3 |
| | b. control | 0.1 | 0 | 0 | 0 | 0 |
| IX | a. neomycin sulfate | 0.8 | 0.7 | trace | — | — |
| | b. control | 0 | 0 | 0 | — | — |
| X | a. streptomycin sulfate | trace | trace | 0 | — | — |
| | b. control | trace | 0 | 0 | — | — |
| XI | a. potassium penicillin | trace | 0 | — | — | — |
| | b. control | 0 | 0 | — | — | — |

In the above Examples VIII–XI, tissue reaction to the coated sutures was not significantly different from that generated by the untreated control suture.

The preceding Examples illustrate the high level of antimicrobial activity which may be retained by sutures of the present invention in the presence of water and during residence in tissue. In each example, the antimicrobial activity of similarly impregnated but uncoated controls was less durable than the coated sutures. The preceding examples also illustrate that different antimicrobial agents demonstrate different levels of persistence in antimicrobial activity.

The present invention broadly encompasses multifilament sutures which are impregnated with an antimicrobial material and top-coated with a segmented polyurethane. The preceding description and examples describe and illustrate preferred embodiments of the invention, and many variations therein will be apparent to those skilled in the art. For example, combinations of antimicrobial agents may be used to impregnate the suture, especially combinations having different retention properties. While it is generally preferred to dry the suture after impregnation and before coating, the drying step may be omitted in some systems. Antimicrobial agents may also be incorporated in the coating, and the coating may be pigmented or dyed to identify the treated suture. All these and other variations which embody the basic concepts of the present invention are accordingly included in the invention.

What is claimed is:

1. A surgical suture exhibiting antimicrobial properties comprising a multifilament suture strand impregnated with an antimicrobial agent and its entire surface coated with a substantially continuous layer of a segmented polyurethane, said polyurethane initially being free of antimicrobial agent.

2. A suture of claim 1 wherein the antimicrobial agent is soluble in a solvent which is compatible with both the antimicrobial agent and the suture.

3. A suture of claim 2 wherein the antimicrobial agent is water or alcohol soluble.

4. A suture of claim 1 wherein the antimicrobial agent is anionic, cationic, or nonionic.

5. A suture of claim 1 wherein the antimicrobial agent is selected from the group consisting of tetracycline hydrochloride, neomycin sulfate, chloramphenicol, streptomycin sulfate, potassium penicillin, polymixin B sulfate, oxytetracycline hydrochloride, gentamycin sulfate, sodium cephalothin, nitrofurazone, rifamycin, benzethonium chloride, sodium oxacillin, dihydrostreptomycin sulfate, disodium carbenicillin, and sodium furadantin.

6. A suture of claim 1 wherein the concentration of antimicrobial agent impregnating the suture is from about 0.2 to 5 percent by weight of suture.

7. A suture of claim 1 wherein the multifilament suture is a braided, twisted, or covered suture.

8. A suture of claim 1 wherein the multifilament suture is a silk, cotton, linen, polyolefin or polyester suture.

9. A suture of claim 1 wherein the layer of segmented polyurethane comprises from about 5 to 10 percent of the weight of the suture.

10. A suture of claim 1 wherein the segmented polyurethane is a spandex type polymer.

11. A suture of claim 10 wherein the segmented polyurethane is comprised of soft segments derived from polymers having a melting point below about 50° C and a molecular weight above about 600, and hard segments derived from polymers having a melting point above about 200° C and a molecular weight in the fiber forming range.

12. A suture of claim 11 wherein the segmented polyurethane is derived from the reaction of a polytetramethylene ether glycol of a molecular weight about 1800 with p,p′-methylenediphenyl diisocyanate in a ratio of about 1.7 moles of diisocyanate per mole of polyether glycol, to form a prepolymer and the prepolymer is extended with about a stoichiometric amount of a mixture of about 80 mole percent ethylenediamine and 20 mole percent 1,3-cyclohexylenediamine and about 7 mole percent diethylamine.

13. A method for preparing an antimicrobial suture comprising the steps of
 a. impregnating the suture with a solution of an antimicrobial agent;
 b. coating the entire surface of the impregnated suture with a solution of a segmented polyurethane polymer in a solvent, said solution being substantially free of antimicrobial agent; and c. drying the coated suture to remove the solvent and provide the impregnated suture with a substantially continuous covering of segmented polyurethane polymer.

14. A method of claim 13 wherein the impregnated suture contains from 0.2 to about 5 percent by weight of antimicrobial agent.

15. A method of claim 13 wherein the coated suture contains from about 5 to 10 percent by weight of segmented polyurethane polymer.

16. A method of claim 13 wherein the impregnated suture is dried prior to coating with said polyurethane polymer.

* * * * *